(12) United States Patent
Stonecipher

(10) Patent No.: US 11,541,168 B2
(45) Date of Patent: Jan. 3, 2023

(54) DRUG DELIVERY DEVICE WITH MESSAGING LABEL

(71) Applicant: AMGEN INC., Thousand Oaks, CA (US)

(72) Inventor: Brian Stonecipher, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 157 days.

(21) Appl. No.: 16/092,248

(22) PCT Filed: Mar. 1, 2017

(86) PCT No.: PCT/US2017/020077
§ 371 (c)(1),
(2) Date: Oct. 9, 2018

(87) PCT Pub. No.: WO2017/189089
PCT Pub. Date: Nov. 2, 2017

(65) Prior Publication Data
US 2019/0192766 A1 Jun. 27, 2019

Related U.S. Application Data

(60) Provisional application No. 62/329,255, filed on Apr. 29, 2016.

(51) Int. Cl.
*A61M 5/142* (2006.01)
*G09F 3/02* (2006.01)

(52) U.S. Cl.
CPC ............... *A61M 5/14248* (2013.01); *A61M 2005/14252* (2013.01); *A61M 2205/33* (2013.01);
(Continued)

(58) Field of Classification Search
CPC .... A61M 5/14248; A61M 2205/14252; A61M 2205/33; A61M 2205/50; A61M 2205/583; G09F 2003/0202; G09F 2003/0208
See application file for complete search history.

(56) References Cited

U.S. PATENT DOCUMENTS

2001/0056258 A1* 12/2001 Evans ................. G06F 19/3468
604/131
2002/0120236 A1 8/2002 Diaz et al.
(Continued)

FOREIGN PATENT DOCUMENTS

WO   WO-2015126721 A1   8/2015

OTHER PUBLICATIONS

"Overlay Panels" TLF Graphics, Inc., Apr. 10, 2015, https://web.archive.org/web/20150410203920/http://www.tlfgraphics.com/overlay.html[Dec. 8, 2020 (Year: 2015).*
(Continued)

*Primary Examiner* — James D Ponton
(74) *Attorney, Agent, or Firm* — Marshall, Gerstein & Borun LLP

(57) ABSTRACT

A drug delivery device includes a housing, a reservoir, a cannula, one or more light sources, a label, and a controller. The reservoir is disposed within the housing. The cannula is
(Continued)

connected to the reservoir for delivering a drug from the reservoir to the patient. The light sources are disposed adjacent the exterior surface of the housing, and each serves to indicate one of one or more operational conditions of the device. The label is fixed to the housing adjacent the light sources, and includes one or more informational messages. Each informational message is aligned with one of the light sources for conveniently conveying to a user an operational condition of the device as indicated by the corresponding light source. Finally, the controller is operably connected to the reservoir and the light sources. The controller is configured to actuate the reservoir to deliver the drug, and to selectively illuminate the one or more light sources based on the operational condition of the drug delivery device.

17 Claims, 2 Drawing Sheets

(52) U.S. Cl.
CPC ... *A61M 2205/50* (2013.01); *A61M 2205/583* (2013.01); *A61M 2209/00* (2013.01); *G09F 2003/0202* (2013.01); *G09F 2003/0208* (2013.01)

(56) References Cited

U.S. PATENT DOCUMENTS

| | | | |
|---|---|---|---|
| 2002/0125894 A1* | 9/2002 | Madsen | G01R 31/58 324/538 |
| 2008/0059133 A1* | 3/2008 | Edwards | A61M 15/009 703/7 |
| 2009/0128330 A1* | 5/2009 | Monroe | A61B 90/98 340/568.1 |
| 2009/0143745 A1* | 6/2009 | Langan | G09F 3/0288 604/189 |
| 2010/0309012 A1 | 12/2010 | Edwards et al. | |
| 2011/0166512 A1* | 7/2011 | Both | A61M 5/14248 604/67 |
| 2012/0010594 A1* | 1/2012 | Holt | A61M 5/14248 604/506 |
| 2014/0358111 A1 | 12/2014 | Brewer et al. | |
| 2017/0049960 A1* | 2/2017 | Nguyen | A61M 5/1452 |

OTHER PUBLICATIONS

International Search Report for International Application No. PCT/US2017/020077, dated Jun. 22, 2017.
Written Opinion of the International Searching Authority for International Application No. PCT/US2017/020077, dated Jun. 22, 2017.

* cited by examiner

DRUG DELIVERY DEVICE WITH MESSAGING LABEL

CROSS-REFERENCE TO RELATED APPLICATIONS

This is the United States national phase of International Patent Application No. PCT/US17/20077, filed Mar. 1, 2017, which claims priority to U.S. Provisional Application No. 62/329,255, filed Apr. 29, 2016, and the entire contents of each which are hereby incorporated herein by reference.

FIELD OF THE DISCLOSURE

The present disclosure is directed to a drug delivery device and, more particularly, to a wearable drug delivery device such as an on-body injector.

BACKGROUND

Injectable drugs are conventionally administered through the use of a needle attached to a syringe having a plunger and a barrel. The needle is inserted to the appropriate depth (e.g., subcutaneous, intradermal, or intramuscular), and the plunger is moved within the barrel to eject the drug into the patient. Many times, the patient will be required to self-administer a drug, in which case the patient is responsible for filling the syringe with the drug, and then injecting the drug into themselves.

When dealing with certain diseases, a patient may have to administer one injection or a series of injections throughout the course of the day. For example, a patient with diabetes may have to administer a number of fast-acting insulin injections before meals, as well as a long-acting insulin injection before bedtime. There are issues that can arise when this many injections are administered in a day, including the potential for the patient to lose track of or forget to administer one or more of the injections. In other cases, the patient may suffer from a different disease such as cancer, where self-injection may not be as frequent but may be complicated by patient fatigue and stress.

To address the issues posed by self-administration, patients often resort to pumps or automatic injection devices. Pumps or automatic injectors may be implanted surgically, although some are designed to be strapped on or attached externally to the patient. These may also be referred to as wearable injectors or on-body injectors. Any of such devices may have a microprocessor that follows an internal program to administer a drug to the patient at the appropriate time. With such devices, it can be important for the patient or caregiver overseeing the self-injection to understand the operational condition of the device at any given time, such as whether the device is preparing to deliver the drug, currently delivering the drug, finished delivering all of the stored drug, malfunctioning, etc.

Some devices therefore include feedback mechanisms for conveying information about the operational condition of the device to the user. Feedback mechanisms can take the form of visual indicators, tactile indicators, etc. But to ensure utility, each user must be properly educated on what the different forms of feedback mean.

SUMMARY

One aspect of the present disclosure includes a drug delivery device having a housing, a reservoir, a cannula, one or more light sources, a label, and a controller. The housing has an interior surface and an exterior surface, the interior surface defining an interior space. The reservoir is disposed within the interior space of the housing, and is configured to store a volume of a drug to be delivered to a patient. The cannula is operably connected to the reservoir and adapted to extend at least partially beyond the exterior surface of the housing for delivering the drug to the patient. The one or more light sources is disposed adjacent the exterior surface of the housing, each light source operable to indicate one of one or more operational conditions of the drug delivery device. The label is fixed to the exterior surface of the housing adjacent to the one or more light sources, and includes one or more informational messages. Each informational message is aligned with one of the one or more light sources for conveying to a user an operational condition of the drug delivery device as indicated by the corresponding light source. Finally, the controller is operably connected to the reservoir and the one or more light sources. The controller is configured to actuate the reservoir to deliver the drug, and to selectively illuminate the one or more light sources based on the operational condition of the drug delivery device.

Another aspect of the present disclosure includes a method of manufacturing a drug delivery device having a housing, a reservoir for storing a volume of a drug, a cannula operably connected to the reservoir for delivering the drug to a patient, one or more light sources for indicating one or more operational states of the drug delivery device, and a controller for controlling operation of at least the reservoir and the light sources. The method includes positioning at least portions of the reservoir, cannula, and controller into an interior space of the housing. The method also include closing the housing such that at least portions of each of the one or more light sources is disposed outside of the housing. The method also includes selecting a label including one or more informational messages. The method further includes applying the selected label to an exterior surface of the housing such that each informational message of the label is aligned with one of the one or more light sources for conveying to a user an operational condition of the drug delivery device as indicated by the corresponding light source.

DETAILED DESCRIPTION OF THE DRAWINGS

Although the following text sets forth a detailed description of different versions of the invention, it should be understood that the legal scope of the invention is defined by the words of the claims set forth at the end of this patent. The detailed description is to be construed as exemplary only and does not describe every possible version of the invention because describing every possible version would be impractical, if not impossible. Numerous alternative versions could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Structural and Functional Overview

Figure 1:
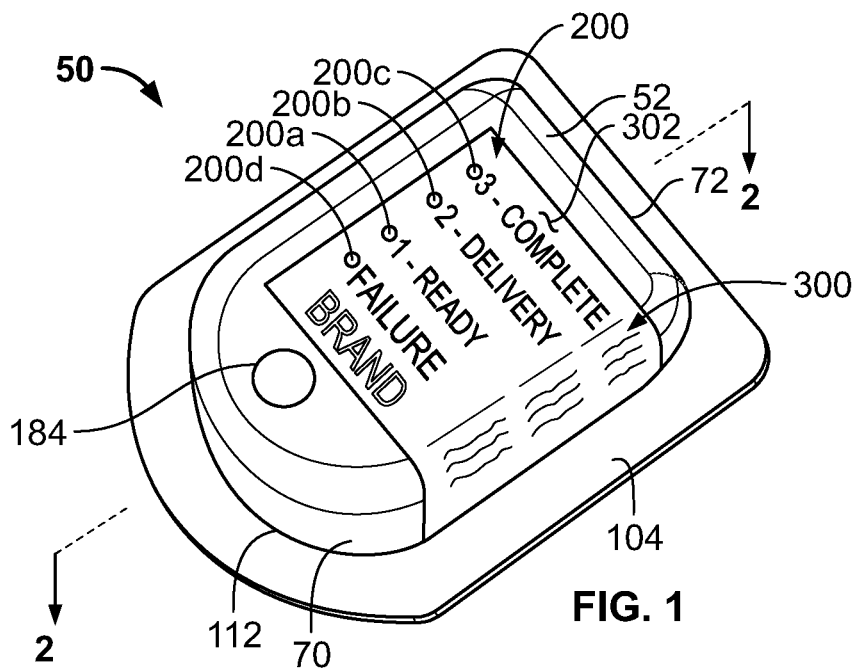
FIG. 1 is a perspective view of a drug delivery device constructed in accordance with the principles of the present disclosure.

FIG. 1 illustrates a wearable drug delivery device 50 according to the present disclosure equipped with one or more light sources 200 for signaling different operational conditions of the device 50 and a label 300 for conveniently conveying the meaning of those light sources 200. The presently disclosed version of the drug delivery device 50 includes first through fourth light sources 200a, 200b, 200c, 200d. Specifically, as will be described below, each of the light sources 200 is configured to illuminate depending on the operational condition of the drug delivery device 50, and the label 300 provides the user with information describing the operational condition indicated. The light sources 200 could all be the same color, all be different colors, or some the same and one or more different. Additionally, the light sources 200 could all be the same size, all be different sizes, or some the same and one or more different. Moreover, when each of the one or more of the light sources 200 is illuminated, this may include providing a solid illumination state where the light source is continuously "on" or may include a blinking state wherein the light source blinks between "on" and "off" according to a fixed frequency or some pattern, such as an ascending or descending frequency pattern to convey to the user some information about the particular operational condition in process. For example, in one version, a slow blinking light source may indicate the beginning of a particular condition, while a fast blinking light source may indicate the approach of the end of that particular condition. Other patterns and frequencies may convey other information. Providing the label 300 with the descriptive information advantageously enables easy customization of the drug delivery device 50 for different markets, languages, products, etc. While the figures of the present disclosure and the following description focus primarily on a wearable device and, particularly an on-body injector, this is only an example. The present disclosure also applies to other wearable drug delivery devices such as pumps, for example, and other drug delivery devices that are not necessarily wearable such as auto-injectors, for example. Other devices are also contemplated.

Figure 2:
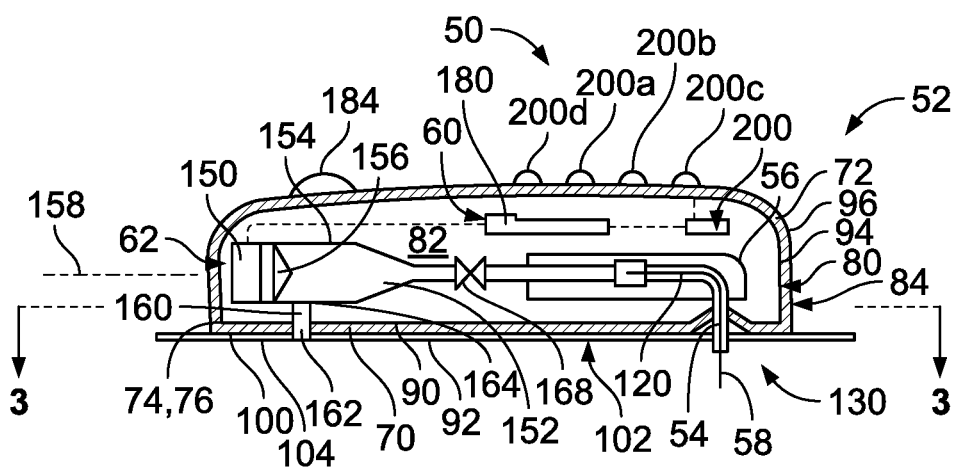
FIG. 2 is a cross-sectional side view of the drug delivery device of FIG. 1.
Figure 3:
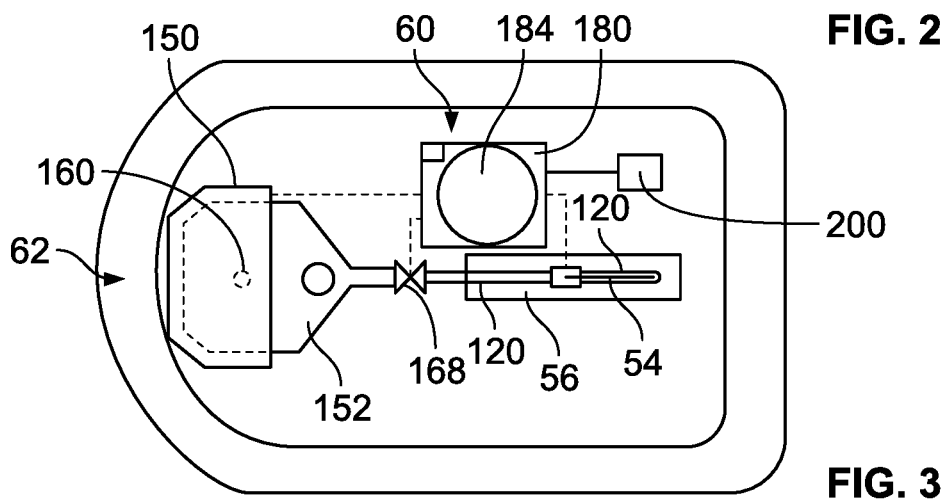
FIG. 3 is a plan view of internal components of the drug delivery device of FIG. 1.

In further detail depicted in FIGS. 1-3, the disclosed drug delivery device 50 has a housing 52 that is adapted to be attached to a patient with an adhesive, for example. As seen in FIGS. 2 and 3, a needle 54 and injector 56 are disposed in the housing 52, and the needle 54 is configured to have a retracted state (not shown), wherein a pointed end 58 is withdrawn inside the housing 52, and a deployed state (FIG. 2), wherein the pointed end 58 projects from the housing 52. Thus, during operation, the injector 56 moves the needle 54 from the retracted state to the deployed state. The device 50 also includes a controller 60 that is coupled to the injector 56 and a reservoir 62 containing a volume of a drug. The controller 60 operates the injector 56 to move the needle 54 between the retracted and deployed positions, and also mechanics associated with the reservoir 62 to deliver the volume of the drug to the patient. Furthermore, the controller 60 is operably connected to the light sources 200 to selectively illuminate the same, as needed.

According to the present disclosure, one illustrative method of operation of the device 50 described above is configured to deliver a single bolus at a particular moment after a predetermined time period has elapsed. First, the device 50 is adhered to the skin of a patient, most likely, but not exclusively, after being placed there by a healthcare provider or the patient him/herself. Typically, this first includes the healthcare provider or the patient removing a backing layer 104 from the device 50. Then, after activation, the device 50 automatically injects the pointed end 58 of the needle 54 from a sealed space defined by the housing 52 of the delivery device 50 into the patient according to programming of the controller 60. Additionally, in this illustrative method, the device 50 automatically determines that a preselected time period has elapsed according to the programming of the controller 60, the predetermined time period being programmed into the controller 60 before the controller 60 is disposed in the space. Further, the device 50 automatically actuates the injector 56 to cause the reservoir 62 to deliver the drug to the patient as a single bolus via the needle 54. Based on the foregoing process, the controller 60 would illuminate the light sources 200 on the device 50 in FIG. 1 in the following sequence. After attachment to the patient and activation, but before delivery, the first light source 200a would illuminate by itself adjacent to the informational message "1—READY." The remaining second through fourth light sources 200b, 200c, 200d would remain off. This indicates that the device 50 is ready to inject. Once injection begins, the first light source 200a turns off and the second light source 200b illuminates adjacent to the informational message "2—DELIVERY." This indicates that drug delivery is in process. Finally, once delivery is complete, light source the second 200b turns off and the third light source 200c illuminates adjacent to informational message "3—COMPLETE." This indicates that the drug has been completely delivered from the device 50 and the device 50 can be removed from the patient. Also shown in FIG. 1, the device 50 includes the fourth light source 200d located adjacent to the informational message "FAILURE." This light source 200d would illuminate at any point during the process if the device is not working properly. Illumination of this fourth light source 200d may prompt the user to reactivate the device 50, immediately remove the device 50, telephone a healthcare provider, or take some other step.

Detailed Structure of Delivery Device

Having thus described the device 50 and its use in general terms, the structure and operation of the device 50 is now described in greater detail. In some versions, the drug delivery device can be constructed and operate in a manner identical to that which is disclosed in U.S. Pat. No. 9,061,097, the entirety of which is incorporated by reference herein. FIG. 1 illustrates the housing 52, which may be made of a plastic material, for example. As seen in FIG. 2, the housing 52 may be defined by two sections, a plate 70 that is applied against the wearer's skin, and a dome 72 that is attached to the plate 70, preferably by a seal at an interface between a peripheral edge 74 of the plate 70 and a peripheral edge 76 of the dome 72.

The housing 52 has an interior surface 80 defining a sealed space 82 and an exterior surface 84. In particular, the plate 70 has an interior surface 90 and an exterior surface 92, and the dome 72 has an interior surface 94 and an exterior surface 96. According to the illustrated embodiment, the interior surface 80 of the housing 52 is defined by the interior surfaces 90, 94 of the plate 70 and the dome 72, while the exterior surface 84 of the housing 52 is defined by the exterior surfaces 92, 96 of the plate 70 and dome 72.

As noted above, the housing 52 is adapted to be attached to the skin of the wearer. In particular, an adhesive may be used. The adhesive is adapted to releasably secure the housing 52 to skin. The adhesive is disposed in a layer 100 on a portion 102 of the exterior surface 84 of the housing 52, and in particular on the exterior surface 92 of the plate 70. The adhesive is covered with the aforementioned backing layer 104, which is removed prior to application of the housing 52 to the skin of the wearer.

As noted above, the device 50 includes the needle 54 with the pointed end 58. The needle 54 may otherwise be referred to as a cannula, which generically includes (a) a rigid hollow needle, (b) a soft hollow catheter, (c) a rigid solid needle and a soft hollow catheter, or (d) a rigid hollow needle and a soft hollow catheter. The needle 54 has a retracted state wherein the pointed end 58 of the needle 54 is withdrawn inside of the space 82 defined by the housing 52. The needle 54 also has a deployed state (illustrated in FIG. 2) wherein the pointed end 58 of the needle 54 projects from the space 82 beyond the exterior surface 84 of the housing 52. As mentioned, the needle 54 may include a rigid needle used in conjunction with a soft hollow catheter 120, the needle 54 being used to insert the catheter 120 into the patient, and then immediately retracted leaving only the catheter behind. So configured, the drug passes through the catheter 120 and into the patient during administration.

As illustrated in FIG. 2, the housing 52 (specifically the plate 70) may have an aperture or opening 130 formed therein to permit the needle 54 (and catheter 120) to pass therethrough. According to certain embodiments (e.g., FIG. 2), the aperture 130 may be unobstructed, such that there is no impediment or obstacle to the movement of the needle 54 (and catheter 120) through the opening 130. However, to better maintain the sterility of the needle 54 and the device's container closure integrity (CCI), a septum or a shield (not shown) may be disposed in or over the aperture 130, or within the space 82 defined by the housing 52 so as to overlie the opening 130.

Still referring to FIGS. 2 and 3, the disclosed version of the device 50 includes the aforementioned injector 56. The injector 56 is coupled to the needle 54 to move the needle 54 between the retracted and deployed states. Examples of exemplary injectors may be found in U.S. Pat. Nos. 7,144,384 and 7,128,727, which patents are incorporated by reference herein for all purposes. The reservoir 62 is also disposed within the space 82 and in selective fluid communication with the needle 54. The reservoir 62 contains or is adapted to contain a volume of a drug. According the illustrated embodiment, the reservoir 62 may include a pump 150 and a reservoir 152.

According to an embodiment of the present disclosure, the reservoir 152 and pump 150 may be defined in part by a combination of a rigid-walled cylinder 154 and a plunger 156 fitted to move along a longitudinal axis 158 of the cylinder 154. The movement of the plunger 156 may be caused by the operation of a gear train that is connected to a motor, according to one variant. Other similar mechanisms for moving the plunger along the cylinder may be found in U.S. Pat. Nos. 7,144,384; 7,128,727, 6,656,159 and 6,656,158, which patents are incorporated by reference herein for all purposes.

According to other variants, a non-rigid collapsible pouch may be substituted for the rigid-walled cylinder 154 and the plunger 156. It will be recognized that where the reservoir 152 is in the form of a non-rigid collapsible pouch, a spring-based mechanical system may be used to compress and pressurized the reservoir. According to still further variants, a non-mechanical system may be used to move the plunger 156 or compress the bag. For example, a gas-generating system may be used, including a two-component system wherein the components are kept apart until the gas is to be generated, in which case they are combined. As a further alternative, a swellable gel may be used, wherein the introduction of water from a source internal to the device causes the gel to increase in dimension to move the plunger or compress the pouch. Examples of such alternative mechanisms may be found in U.S. Pat. Nos. 5,957,895; 5,858,001; and 5,814,020, which patents are incorporated by reference herein for all purposes.

Further, the delivery device 50 may include a fill port 160 in fluid communication with the reservoir 152, the fill port 160 having an inlet 162 disposed on the exterior surface 84 of the housing 52. The inlet 162 may be adapted to receive a Luer tip of a syringe, although a piercable rubber septum may be used instead, for example. The fill port 160 may also include a cover disposed in the inlet 162 to close the fill port 160. An outlet 164 of the fill port 160 is connected to the reservoir 152. One or more filters may be disposed between the inlet 162 and the outlet 164 to limit the passage of air or particulate matter into the reservoir 152 along with the drug. In use, the healthcare provider may inject the drug through the fill port 160 into the reservoir 152. In other versions, the reservoir 152 may be pre-filled such that the device 50 does not require the fill port and the healthcare provider or patient need not fill the reservoir with a syringe.

In addition, the reservoir 62 may include a pinch valve 168 or other type of valve disposed between the reservoir 152 and the needle 54. The inclusion of the valve 168 permits greater control of the timing of the delivery of the drug. Other devices, such as flow regulators, may be disposed in the flow path between the reservoir 152 and the patient to control the flow of the drug therebetween.

The controller 60, as mentioned above, is coupled to the injector 56 and the reservoir 62. The controller 60 is programmed to control the injector 56 and the reservoir 62 to carry out certain activities and to control the light sources 200. The controller 60 is disposed within the sealed space 82 defined within the disposable housing 52 and programmed prior to being disposed within the sealed space 82. Thus, in some embodiments, once the controller 60 is disposed in the space 82 and the housing 52 is sealed, the controller 60 may not be reprogrammed.

According to one embodiment, the controller 60 may include a programmable microprocessor 180 and a power supply (not shown) coupled to the microprocessor 180. The power supply may include one or more batteries. Alternatively, the controller 60 may be a mechanical device, a combination of mechanical devices, a combination of electrical devices (hard-wired circuits or circuit components), or a combination of mechanical and electrical devices.

For instance, in the illustrative operational method described above, the controller 60 must determine that a predetermined time period has elapsed. The controller may be programmed to perform this action by accessing a timer circuit or a timer function within the microprocessor 182. Alternatively, in a mechanical controller, the timer may refer instead to a clockwork mechanism, a spring-driven timer, or a dashpot timer. A benefit of the use of a mechanical controller utilizing a mechanical timer would be the elimination of batteries, making the device more environmentally friendly for purposes of disposal.

A number of different mechanisms may be used to initiate the operation of the controller 60 to that it carries out its programming. According to an exemplary embodiment of the actuation mechanism, a single button 184 may be coupled to the controller 60. The button 184 may be disposed so that it depends through the exterior surface 84 of the housing 52, and the controller 60 may be responsive to actuation of the button 184 (e.g., depression of the button 184) to initiate the controller program.

The controller 60 can be programmed to actuate the injector 56 to move the needle 54 from the retracted state to the deployed state only once. The controller 60 can be also programmed to determine that a preselected time period has elapsed only once. Further, the controller 60 can be programmed to actuate the drug supply to deliver the volume of the drug to the patient as a single bolus.

In one exemplary version, the controller 60 may be programmed to determine that a twenty-four hour period has elapsed after actuation of the button 184. Further, the controller 60 may be programmed to actuate the reservoir 62 to deliver the volume of the drug to the patient as a single bolus in less than thirty minutes. In fact, the controller 60 may be programmed to actuate the reservoir 62 to deliver the volume of the drug to the patient as a single bolus in less than six seconds. In an embodiment wherein the reservoir 62 includes a valve 168, the controller 60 may be programmed to open the valve 168 prior to actuating the remainder of the reservoir 62 to deliver the volume of the drug.

The controller 60 may also be programmed to cause other actions to occur. Specifically, as discussed above, the controller 60 of the present device 50 is coupled to the one or more light sources 200. In other embodiments, the light sources 200 could include alternative visual indicators driven by the controller 60. The light sources 200 as described above are used in conjunction with the label 300 to signal to the healthcare provider or the patient that the controller 60 is operating according to a specific operating condition. For example, the controller 60 may control the light sources 200, each of which may be a light emitting diode (LED) for example, to signal to the patient that the device 50 is READY for injection, that drug DELIVERY has begun, and that drug delivery is COMPLETE.

Detailed Structure of the Label

Figure 4:
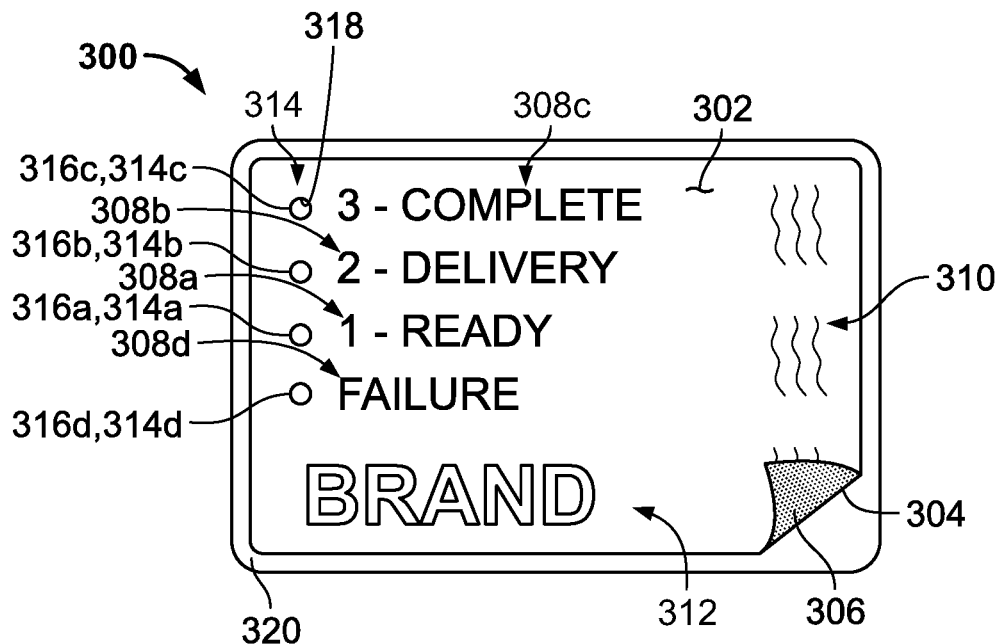
FIG. 4 is a plan view of one version of a label of the drug delivery device of the present disclosure.

FIG. 4 depicts one version of the label 300 prior to application to the drug delivery device 50, and being disposed on a backing layer 320, with the lower right-hand corner curled up for illustration only. As can be seen, this version of the label 300 includes a generally rectangular shaped piece of flexible material, which could be a paper material, a polymer material, a film, a composite material, or other suitable material. In some embodiments, the label 300 may constitute a component of the housing 52 itself and can include a more rigid plastic material. The label 300 of the disclosed embodiment includes an exterior surface 302 and an interior surface 304. At least a portion of the interior surface 304 can be coated with an adhesive 306 such that the label 300 can be attached to the exterior surface 96 of the dome 72 of the drug delivery device 50, as depicted in FIG. 1. When attached to the drug delivery device 50, the exterior surface 302 faces away from the device 50. In some embodiments, the adhesive 304 can include a releasable adhesive such that the label 300 can be removably attached to the drug delivery device 50, or the adhesive 304 can be a permanent adhesive such that the label 300 cannot be removed from the drug delivery device 50 without substantial energy potentially degrading and/or destroying the adhesive and/or the material from which the label 300 is constructed.

The depicted version of the label 300 further includes one or more informational messages 308, one or more regulatory messages 310, and one or more branding messages 312, each for conveying information to the user of the device 50.

The one or more regulatory messages 310 can include textual regulatory compliance information relative to the product to be administered by the drug delivery device 50 and/or relative to the drug delivery device 50 itself. The one or more branding messages 312 can include textual, graphic, symbolic or other information regarding the source or the brand of the product to be administered by the drug delivery device 50 and/or the source or the brand of the drug delivery device 50 itself, for example. Moreover, in this specific version, the label 300 includes a first informational message 308a, a second informational message 308b, a third informational message 308c, and a fourth informational message 308d. Each of the first through fourth informational messages 308a-308d are configured on the label 300 to correspond to one of the first through fourth light sources 200a-200d of the drug delivery device 50 when the label 300 is applied to the drug delivery device 50. As such, in the present version of the label 300, the first informational message 308a reads "1—READY," which means that when the adjacent light source 200a is illuminated, the device 50 is in a ready-state condition where it is ready for injection, but not yet injecting. This typically means that the user has successfully applied the device 50 to the patient's skin and depressed the activation button 184. The second informational message 308b reads "2—DELIVERY," which means that when the second light source 200b is illuminated the device 50 is in a delivery-in-process condition where it is actively delivering drug into the patient. The third informational message 308c reads "3—COMPLETE," which means that when the third light source 200c is illuminated the device 50 is in a delivery-complete-condition where drug delivery is complete, and possibly the device 50 can be removed from the patient depending on the type of prescription to which the device 50 relates. Finally, the fourth informational message 308d reads "FAILURE," which means that when the fourth light source 200d is illuminated, the device is in a failure-state condition where an operating error has occurred either with attaching the device 50 to the patient, activating the device 50, delivering the drug, or otherwise. While the various informational messages 308 have thus far included alphanumeric and/or textual messages, in alternative versions the informational messages 308 can also include icons, symbols, images, pictures, etc. or any other visually indicator.

Finally, as depicted in FIG. 4, the label 300 of the present disclosure includes one or more alignment features 314, corresponding to the number of informational messages 308 and light sources 200. As such, the present version includes a first alignment feature 314a, a second alignment feature 314b, a third alignment feature 314c, and a fourth alignment feature 314d. The first alignment feature 314a is positioned adjacent to the first informational message 308a and vice versa. The second alignment feature 314b is positioned adjacent to the second informational message 308b and vice versa. The third alignment feature 314c is positioned adjacent to the third informational message 308c and vice versa. The fourth alignment feature 314d is positioned adjacent to the fourth informational message 308d and vice versa.

In the depicted embodiment of the label 300, the alignment features 314a-314d include openings 316a-316d, which are circular in shape. The openings 316a-316d are defined by contoured edges 318 of the label 300. For clarity, only one contoured edge 318 is expressly identified in FIG. 4. So configured, when the label 300 is applied to the drug delivery device 50, the alignment features 314 align the label 300 relative to the light sources 200. Specifically, in the disclosed embodiment, the openings 316a-316d receive and/or surround the light sources 200a-200d, respectively, such that the first through fourth information messages 308a-308d are properly aligned adjacent to the corresponding first through fourth light sources 200a-200d. Thus, it can be said that when the label 300 is applied to the drug delivery device 50, each of the contoured edges 318 of the alignment features 314 is positioned adjacent to one of the light sources 200.

While the present version of the label 300 includes alignment features 314 comprising circular openings 316, other versions of the label 300 can include alignment features 314 defined by contoured edges 318 that do not define circular openings. For example, in one version, the contoured edges 318 can define arched recesses for partly receiving and/or surrounding the light sources 200 and aligning the label 300 on the drug delivery device 50 relative to the light sources 200. Other configurations are possible.

Figure 5:
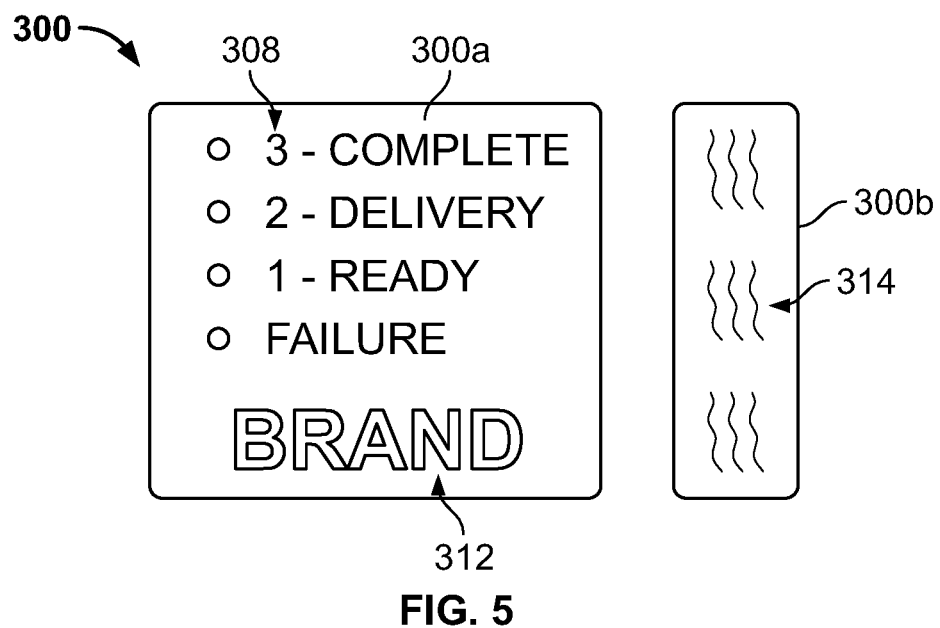
FIG. 5 is a plan view of another version of a label of the drug delivery device of the present disclosure.

While the label 300 in FIGS. 1 and 4 is depicted as a single label, in other versions, the label 300 could include a plurality of sub-labels 300a, 300b, as shown in FIG. 5, for example. In the version depicted in FIG. 5, the informational messages 308 and branding message 312 reside on a first sub-label 300a while the regulatory message 310 resides on a secondary sub-label 300b. This arrangement could be useful where different regulatory messages 310 may be required for the same product, for example, in different jurisdictions with common languages.

The material from which the label 300 is manufactured, as mentioned, could be a paper material, a plastic material, a film, etc. In some versions, the label material may be opaque, translucent, transparent, or other. In versions where the label material may be translucent, transparent, or clear, for example, such that light can pass through the label material, the alignment features 314 may not include cut outs or recesses as described above, but rather, can include portions of the solid label material. In this regard, the same alignment features 314 would be positioned adjacent to (e.g., above or overlaying) the corresponding light sources. Thus, for the purposes of this disclosure, the term adjacent when used in connection with describing the relative location of the label and the light sources includes those labels with portions positioned above or overlaying the light sources such that the light sourced backlight a portion or the entirety of the label. In some versions, the various messages 308, 310, 312 can be printed on the exterior surface 302 of the label 300. In some versions where the label material is transparent, translucent, or clear, for example, one or more of the various messages 308, 310, 312 can be printed on the interior surface 304 of the label 300. In some versions, the informational messages 308 can be printed in a way that when the label 300 is applied to the drug delivery device 50, each of the informational messages 308 is invisible until if and when the correspondingly adjacent light source 200 is activated (e.g., illuminated, charged, energized, etc.), which in turn illuminates the informational message 308. In this configuration, when one light source 200 is illuminated the correspondingly adjacent informational message 308 is illuminated but the others are not. In some versions, this can be accomplished through the type of ink used to print the informational messages 308. For example, the informational messages 308 could be printed in a light activated ink that only becomes visible to the human eye when exposed to a particular wavelength of light emitted by the immediately adjacent light source 200. As can be appreciated, in addition to seeing an illuminated light source 200, the foregoing arrangement of illuminated informational messages 308 may further assist in bringing the user's attention to the appropriate informational message 308. Other mechanisms could also be used to bring the user's attention to the appropriate informational message 308. For example, the light sources 308 may be different sizes based on the importance of the information conveyed. In one version, for example, the fourth light source 308d associated with the failure-state condition could be larger than the other light sources 308, and could optionally be a red color to alert the user of a problem. It should be appreciated that different sizes and/or colors of the light sources 308 can convey different levels of urgency, prompting different emotional responses by the user.

While the drug delivery device 50 described in relation to FIGS. 1 to 5 includes first through fourth light sources 200 and corresponding first through fourth informational messages 308, other versions can have more or less light sources 200 and informational messages 308. For example, in some versions where the drug delivery device 59 must be filled with a pre-filled syringe, the drug delivery device 50 can have a fifth light source associated with a filling-state condition, meaning that when the fifth light source is illuminated, the user is prompted to insert the prefilled syringe into the device 50 and load the reservoir with the drug. The same drug delivery device could optionally include a sixth light source 200 that illuminates upon completion of filling to alert the user to depress the activation button 184. Thus, it should be appreciated that the four light sources 200 and corresponding informational messages 308 described herein are merely exemplary and variations are within the scope of the disclosure.

Method of Manufacture

One advantage of the disclosed configuration is that the label 300 can be printed in many different languages and with varied branding and/or regulatory messages for application to drug delivery devices 50 for use in various global markets. This can result in cost savings relative to systems where the housing 52 of the drug delivery device 50 directly carries the informational, regulatory and/or branding messages 308, 310, 312 because it is less costly to maintain inventory of different labels 300 printed for various markets than it is to maintain inventory of different housings 52. Moreover, should a change in one or more of the messages be required, new labels 300 for inventory can easily be printed without substantial time or cost requirements. Finally, this arrangement could even make real-time label 300 printing possible.

Thus, it should be appreciated that one advantageous method of manufacturing a drug delivery device 50 according to the present disclosure would include first assembling the internal components of the device 50 into the housing 52. This might include positioning at least portions of the reservoir 62, the needle (i.e., cannula) 54, and controller 60 into the interior space 82 of the housing 52. Then, the dome 72 is coupled to the plate 70 to close the housing 52. Because the light sources 200 must be exposed outside of the housing 52, one version of the drug delivery device 50 includes a number of corresponding openings in the dome 72 such that the light sources 200 pass through or are at visible through the openings. In other version, the dome 72 may have a single opening through which all of the light sources 200 are visible when illuminated. In versions where the light sources 200 do not extend out through the dome 72, any openings in the dome may be covered by one or more windows. In other versions, the light sources 200 are simply pre-fixed to the exterior surface 96 of the dome 72.

Once the housing 52 is closed and optionally sealed, a label 300 is selected and ultimately applied to the housing 52 such that the informational messages 308 carried by the label 300 are aligned with the light sources 200 for conveying the appropriate operational condition to the user. In addition to selecting the label 300, some versions of the method include selecting the specific language from a plurality of available languages in which one or more of the various messages 308, 310, 312 on the label 300 is provided. Moreover, the manufacturing process can include selecting a regulatory and/or a branding message from a plurality of available regulatory and/or branding messages, respectively. In some versions, the manufacturing process includes selecting a label 300 from a plurality of available labels 300 stored in inventory, wherein the plurality of available labels 300 incudes different labels having different pre-printed languages and/or messages 308, 310, 312 In other versions, after the language and/or messages 308, 310, 312 are selected, the manufacturing process includes printing the selected label 300 in real-time. In those versions of the drug delivery device 50 having a label 300 with a plurality of sub-labels, the manufacturing process can further include selecting each of the sub-labels 300a, 300b. For example, in one situation, both the primary and secondary 300a, 300b sub-labels may be in the same language, but the second sub-label 300b carrying the regulatory message 310 might have to be customized and/or selected for a different and specific market.

After the label 300 has been selected, the manufacturing process can include removing the backing layer 320 (shown in FIG. 4) from the label 300, thereby exposing the adhesive 306 carried on the interior surface 304 of the label 300. With the adhesive 306 exposed, the label 300 is then applied to the housing 52 as illustrated in FIG. 1. As the label 300 is applied, the alignment features 314 should be positioned relative to the respective light sources 200. In the version of the label 300 disclosed above, this includes positioning the openings 316 around the light sources 200 such that the contoured edges 318 are adjacent to the light sources 200.

The above description describes various systems and methods related to a drug delivery device. It should be clear that the system, drug delivery device or methods can further comprise use of a medicament listed below with the caveat that the following list should neither be considered to be all inclusive nor limiting. The medicament will be contained in the reservoir of the drug delivery device. In some instances, the reservoir is the primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858) as well as erythropoietin molecules or variants or analogs thereof as disclosed in the following patents or patent applications U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667;

WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713 including OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4.

Myostatin binding proteins, peptibodies, and related proteins, and the like, including myostatin specific peptibodies, particularly those described in U.S. Publication No. 2004/0181033 and PCT Publication No. WO 2004/058988, particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631.

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1.

Interleukin 1-receptor 1 ("IL1-R1") specific antibodies, peptibodies, and related proteins, and the like, including but not limited to those described in U.S. Publication No. 2004/097712, in parts pertinent to IL1-R1 specific binding proteins, monoclonal antibodies in particular, especially, without limitation, those designated therein: 15CA, 26F5, 27F2, 24E12, and 10H7.

Ang2 specific antibodies, peptibodies, and related proteins, and the like, including but not limited to those described in PCT Publication No. WO 03/057134 and U.S. Publication No. 2003/0229023, particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein.

NGF specific antibodies, peptibodies, and related proteins, and the like including, in particular, but not limited to those described in U.S. Publication No. 2005/0074821 and U.S. Pat. No. 6,919,426, particularly as to NGF-specific antibodies and related proteins in this regard, including in particular, but not limited to, the NGF-specific antibodies therein designated 4D4, 4G6, 6H9, 7H2, 14D10 and 14D11.

CD22 specific antibodies, peptibodies, and related proteins, and the like, such as those described in U.S. Pat. No. 5,789,554, as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof.

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11Al2, PINT-12A1, PINT-12A2, PINT-12A3, PINT-12A4, and PINT-12A5, as described therein, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein).

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, particularly as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, particularly as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, as disclosed in the foregoing publication and in Thakur et al. (1999), Mol. Immunol. 36:1107-1115. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos.

2003/0195156 and 2006/0135431, particularly as to TALL-1 binding proteins, particularly the molecules of Tables 4 and 5B.

Parathyroid hormone ("PTH") specific antibodies, peptibodies, and related proteins, and the like, such as those described in U.S. Pat. No. 6,756,480, particularly in parts pertinent to proteins that bind PTH;

Thrombopoietin receptor ("TPO-R") specific antibodies, peptibodies, and related proteins, and the like, such as those described in U.S. Pat. No. 6,835,809, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, particularly in parts pertinent to proteins that bind HGF;

TRAIL-R2 specific antibodies, peptibodies, related proteins and the like, such as those described in U.S. Pat. No. 7,521,048, particularly in parts pertinent to proteins that bind TRAIL-R2;

Activin A specific antibodies, peptibodies, related proteins, and the like, including but not limited to those described in U.S. Publication No. 2009/0234106, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, particularly in parts pertinent to proteins that bind TGF-beta;

Amyloid-beta protein specific antibodies, peptibodies, related proteins, and the like, including but not limited to those described in PCT Publication No. WO 2006/081171, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim , G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery device and methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, systems, methods, and their elements.

What is claimed:

1. A drug delivery device comprising:
    a housing having an interior surface and an exterior surface, the interior surface defining an interior space;
    a reservoir disposed within the interior space of the housing, the reservoir configured to store a volume of a drug to be delivered to a patient;
    a cannula operably connected to the reservoir and adapted to extend at least partially beyond the exterior surface of the housing for delivering the drug to the patient;
    one or more light sources disposed adjacent the exterior surface of the housing, each light source operable to indicate one of one or more operational conditions of the drug delivery device;
    an adhesive label fixed to the exterior surface of the housing adjacent to the one or more light sources, the adhesive label including one or more informational messages, each informational message aligned with one of the one or more light sources for conveying to a user an operational condition of the drug delivery device as indicated by a correspondingly adjacent light source of the one or more light sources, wherein the adhesive label includes one or more alignment features to align the adhesive label relative to the one or more light sources; and
    a controller operably connected to the reservoir and the one or more light sources, the controller being configured to actuate the reservoir to deliver the drug, and to selectively illuminate the one or more light sources based on the operational condition of the drug delivery device,
    wherein the one or more alignment features of the adhesive label include one or more openings, each opening receiving one of the one or more light sources, the one or more openings aligning the one or more light sources with the one or more informational messages of the adhesive label, wherein at least one informational message aligned with at least one light source of the one or more light sources includes a textual and/or symbolic message describing a delivery-complete condition of the drug delivery device.

2. The device of claim 1, wherein the one or more light sources comprises at least first through fourth light sources, the first light source corresponding with a failure-state condition of the drug delivery device, the second light source corresponding with a ready-state condition of the drug delivery device, the third light source corresponding with a delivery-in-process condition of the drug delivery device, and the fourth light source corresponding with the delivery-complete condition of the drug delivery device.

3. The device of claim 2, wherein the one or more informational messages comprises first through fourth informational messages, the first informational message aligned with the first light source and including at least a first textual and/or symbolic message describing the failure-state condition, the second informational message aligned with the second light source and including at least a second textual and/or symbolic message describing the ready-state condition of the drug delivery device, the third informational message aligned with the third light source and including at least a third textual and/or symbolic message describing the delivery-in-process condition of the drug delivery device, and the fourth informational message aligned with the fourth light source and including at least a fourth textual and/or symbolic message describing the delivery-complete condition of the drug delivery device.

4. The device of claim 1, wherein the adhesive label further comprises:
   (a) at least one of the following informational messages: (i) a regulatory message, (ii) a branding message;
   (b) a plurality of sub-labels;
   (c) an adhesive label adhered to the exterior surface of the housing; and/or
   (d) an opaque, translucent or transparent label.

5. The device of claim 1, wherein each of the one or more light sources comprises a light-emitting diode.

6. The device of claim 1, wherein a first informational message of the one or more informational messages activates or is backlit upon illumination of the correspondingly adjacent light source.

7. The device of claim 6, wherein a second informational message of the one or more informational messages does not illuminate upon illumination of the light source correspondingly adjacent to the first informational message.

8. The device of claim 1, wherein the adhesive label includes an interior surface and an exterior surface, the interior surface facing the exterior surface of the housing and the exterior surface facing away from the exterior surface of the housing, and wherein the one or more informational messages is printed on either (a) the exterior surface of the adhesive label, or (b) the interior surface of the adhesive label.

9. The device of claim 1, further comprising a drug product stored in the reservoir, wherein the drug product comprises one of: (a) a monoclonal antibody (IgG) that binds human Proprotein Convertase Subtilisin/Kexin Type 9 (PCSK9), (b) a granulocyte colony-stimulating factor (G-CSF), (c) a product that targets or modulates sclerostin, or (d) a product that relates to calcitonin gen-related peptide (CGRP).

10. A method of manufacturing a drug delivery device having a housing, a reservoir for storing a volume of a drug, a cannula operably connected to the reservoir for delivering the drug to a patient, one or more light sources for indicating one or more operational states of the drug delivery device, and a controller for controlling operation of at least the reservoir and the one or more light sources, the method comprising:

positioning at least portions of the reservoir, cannula, and controller into an interior space of the housing;

closing the housing such that at least a portion of each of the one or more light sources is disposed outside of the housing;

selecting an adhesive label including one or more informational messages; and applying the selected adhesive label to an exterior surface of the housing such that each informational message of the adhesive label is aligned with one of the one or more light sources for conveying to a user an operational condition of the drug delivery device as indicated by a corresponding light source, wherein applying the selected adhesive label includes positioning one or more alignment features of the selected adhesive label relative to the one or more light sources, and wherein positioning one or more alignment features of the selected adhesive label includes positioning one or more openings of the selected adhesive label such that the opening receives the one or more light sources and aligning the one or more light sources with the one or more informational messages of the adhesive label by the one or more openings, at least one informational message aligned with at least one light source of the one or more light sources including a textual and/or symbolic message describing a delivery-complete condition of the drug delivery device.

11. The method of claim 10, further comprising selecting:
   (a) at least one language for the adhesive label from a plurality of available languages;
   (b) a regulatory message for the adhesive label from a plurality of available regulatory messages; and/or
   (c) a branding message for the adhesive label from a plurality of available branding messages.

12. The method of claim 10, wherein selecting a an adhesive label includes selecting a label that is pre-printed with at least one of: (a) the one or more informational messages, (b) a selected regulatory message, or (c) a selected branding message.

13. The method of claim 10, further comprising printing on the adhesive label at least one of: (a) the one or more informational messages in at least one selected language, (b) a selected regulatory message in at least one selected language, or (c) a selected branding message.

14. The method of claim 10, wherein selecting the adhesive label comprises:
   (a) selecting a plurality of sub-labels; and/or
   (b) selecting a label that is opaque, translucent, or transparent.

15. The method of claim 10, further comprising removing a backing layer from the selected label prior to applying the selected adhesive label.

16. The method of claim 10, wherein applying the selected label comprises applying an interior surface of the label to face the exterior surface of the housing and an exterior surface of the label facing away from the exterior surface of the housing, and wherein the one or more informational messages is printed on either (a) the exterior surface of the adhesive label, or (b) the interior surface of the adhesive label.

17. The method of claim 10, further comprising at least partly filling the reservoir with one of: (a) a monoclonal antibody (IgG) that binds human Proprotein Convertase Subtilisin/Kexin Type 9 (PCSK9), (b) a granulocyte colony-stimulating factor (G-CSF), (c) a product that targets or modulates sclerostin, or (d) a product that relates to calcitonin gen-related peptide (CGRP).

\* \* \* \* \*